US012514754B2

(12) United States Patent
Krüger et al.

(10) Patent No.: US 12,514,754 B2
(45) Date of Patent: Jan. 6, 2026

(54) SYSTEM COMPRISING AN APPLICATOR AND A STENT FOR A EUSTACHIAN TUBE

(71) Applicants: Bess Pro GmbH, Berlin (DE); Medizinische Hochschule Hannover, Hannover (DE)

(72) Inventors: Philipp Krüger, Berlin (DE); Sven Karsten Lange, Berlin (DE); Thomas Lenarz, Hannover (DE); Gerrit Paasche, Werben/OT Berge (DE); Robert Schuon, Münster (DE)

(73) Assignees: Bess Pro GmbH, Berlin (DE); Medizinische Hochschule Hannover, Hannover (DE)

( * ) Notice: Subject to any disclaimer, the term of this patent is extended or adjusted under 35 U.S.C. 154(b) by 285 days.

(21) Appl. No.: 18/012,567

(22) PCT Filed: Jun. 11, 2021

(86) PCT No.: PCT/DE2021/100501

§ 371 (c)(1),
(2) Date: Dec. 22, 2022

(87) PCT Pub. No.: WO2021/259418

PCT Pub. Date: Dec. 30, 2021

(65) Prior Publication Data

US 2023/0240896 A1 Aug. 3, 2023

(30) Foreign Application Priority Data

Jun. 25, 2020 (DE) ..................... 10 2020 116 795.4

(51) Int. Cl.
*A61F 11/20* (2022.01)
*A61F 2/962* (2013.01)

(52) U.S. Cl.
CPC ............ *A61F 11/202* (2022.01); *A61F 2/962* (2013.01); *A61F 2250/001* (2013.01); *A61F 2250/0096* (2013.01); *A61M 2210/0675* (2013.01)

(58) Field of Classification Search
CPC .. A61F 11/202; A61F 2/962; A61F 2250/001; A61F 2250/0096; A61M 2210/0675
See application file for complete search history.

(56) References Cited

U.S. PATENT DOCUMENTS 6,589,286 B1 * 7/2003 Litner ....................... A61P 7/02 604/8
2002/0013616 A1 1/2002 Carter et al.
(Continued)

FOREIGN PATENT DOCUMENTS

CN 109998747 7/2019
DE 202005022020 9/2012
(Continued)

*Primary Examiner* — Jing Rui Ou
(74) *Attorney, Agent, or Firm* — Henry M. Felereisen LLC

(57) ABSTRACT

A system Includes a stent including a first end for arrangement on a tubal ostium, a second end for arrangement on a bony isthmus of smaller diameter than a diameter of the first end, and adjacent to the second end a length portion of decreasing diameter. The system further includes an applicator for placement of the stent in a Eustachian tube. The applicator has a proximal end for handling the applicator and a distal end for receiving the stent. The distal end includes an inner part which has at least one area that is plastically deformable by manual force, for adaptation to a patient-dependent access angle of the Eustachian tube, and an outer tube which surrounds the inner part at a radial distance and which delimits an annular gap for receiving the stent, with the stent in the annular gap made of nitinol and being self-expanding.

13 Claims, 2 Drawing Sheets

(56) References Cited

U.S. PATENT DOCUMENTS

| | | | | |
|---|---|---|---|---|
| 2003/0139804 | A1 | 7/2003 | Hankh et al. | |
| 2006/0200225 | A1* | 9/2006 | Furst | A61F 2/91 623/1.15 |
| 2007/0043381 | A1 | 2/2007 | Furst et al. | |
| 2009/0209972 | A1* | 8/2009 | Loushin | A61M 31/00 606/109 |
| 2009/0276027 | A1* | 11/2009 | Glynn | A61F 2/95 623/1.13 |
| 2010/0024830 | A1* | 2/2010 | Rousseau | A61F 2/20 623/9 |
| 2010/0174366 | A1* | 7/2010 | Avior | A61F 11/202 623/10 |
| 2010/0198191 | A1* | 8/2010 | Clifford | A61B 8/12 600/249 |
| 2012/0184983 | A1 | 7/2012 | Chang et al. | |
| 2015/0305943 | A1* | 10/2015 | Hossainy | A61M 29/02 604/514 |
| 2018/0001065 | A1 | 1/2018 | Chang et al. | |
| 2019/0060125 | A1 | 2/2019 | Hoo-Chu et al. | |

FOREIGN PATENT DOCUMENTS

| | | |
|---|---|---|
| EP | 1 926 521 | 12/2015 |
| EP | 2 532 300 | 3/2017 |
| WO | WO 2007/022496 | 2/2007 |

* cited by examiner

SYSTEM COMPRISING AN APPLICATOR AND A STENT FOR A EUSTACHIAN TUBE

CROSS-REFERENCES TO RELATED APPLICATIONS

This application Is the U.S. National Stage of International Application No. PCT/DE2021/100501, filed Jun. 11, 2021, which designated the United States and has been published as International Publication No. WO 2021/259418 A1 and which claims the priority of German Patent Application, Serial No. 10 2020 116 795.4, filed Jun. 25, 2020, pursuant to 35 U.S.C. 119 (a)-(d).

BACKGROUND OF THE INVENTION

The invention relates to a system including an applicator and a stent for a Eustachian tube.

Many people suffer from chronic tube ventilation disorders. When the valve function of the auditory tube (Tuba Eustachii—Eustachian tube) is disturbed, the pressure equalization between the middle ear and the environment is no longer sufficiently possible. This leads—apart from discomfort to severe ear pain—to conductive or combined hearing loss, mainly due to inflammatory processes.

The Valsalva maneuver, in which the patient tries to exhale forcefully while pinching the nose shut and closing the mouth for about 10 seconds, as therapeutic methods that are performed repetitively or provided with instrumental aids such as nasal balloons that are inflated through the nose, oftentimes do not ensure permanent adequate middle ear ventilation and drainage, so that a paracentesis or tympanic drainage through a small surgical procedure becomes necessary for sufficient middle ear ventilation. The therapy attacks hereby one of the most sensitive parts of the middle ear: the eardrum. This essential part of the sound conduction chain is normally atrophic and scarred in chronically diseased middle ear. Tympanic drainage is the best therapy available today, however the protective function of the tube is compromised in tympanic drainage.

An interventional method or therapy of the tube itself is known in the meantime as balloon dilatation of the Eustachian tube (BET). Analogous to cardiovascular balloon dilatation in the case of coronary heart disease, the cartilaginous part of the auditory tube is briefly dilated with a balloon catheter. This procedure has shown to be almost completely free of side effects. However, the freedom from side effects is also accompanied with an effectiveness that has not been unequivocally proven. Apparently, a one-time expansion of the already slack tissue structures can only achieve a short-term improvement. In the case of chronic tube disorder, the muscle groups that ensure regular opening and closing of the tube are generally not functional or only barely functional.

In light of the foregoing, the invention is based on the object to provide a possibility to lastingly treat chronic tube ventilation disorders.

SUMMARY OF THE INVENTION

This object is attained by a system as set forth hereinafter.

The subclaims relate to suitable refinements of the invention.

The applicator according to the invention for placing a stent in a Eustachian tube has a proximal end for handling the applicator and a distal end for receiving a stent that can be placed in a Eustachian tube. The particular feature of the applicator is the distal end. It has an inner part and an outer tube. The outer tube surrounds the inner part at a radial distance, so that an annular gap is formed for receiving a stent. The outer tube can be retracted to release a stent arranged in the annular gap for placement. The inner part of the distal end of the applicator is designed to be plastically deformable, at least in some areas, for adaptation to a patient-dependent access angle to the Eustachian tube.

Rigid applicators are not or not sufficiently suitable to take into account the anatomical conditions of the tube. Endoscopes that are flexible at the end are used for balloon dilatation. However, the invention does not provide for a one-time expansion of the already slack tissue structure, but rather to show an applicator that is designed to introduce an elastic stent into the tube in order to ensure a lasting improvement. A stent supports the weak muscles which are required to actively open the Eustachian tube by maintaining increased tension and/or facilitating passive opening of the tube in the event of great pressure differentials. In both cases, the application of a stent to remain in the tube has significant advantages over the one-time or repeatedly required balloon dilatation.

The invention provides a special applicator for this purpose. The applicator has a plastically deformable portion that allows the applicator to conform to the existing human anatomy, in particular to a patient-dependent tube angle. After inserting the applicator into the tube, the stent already loaded in the applicator can be placed at the desired location by actuating a release unit.

At its distal end, the applicator has a bendable area that is not preformed in a specific direction but is malleable by using manual force. Deforming or bending in the desired direction and to the desired extent can be implemented by the user before the procedure in accordance with the anatomy of the patient. Only manual force is required. There is no need for tools. As a result, bending becomes particularly gentle.

The malleable inner part preferably has a length in a range from 20 mm to 40 mm. The stent to be applied preferably has a length of 8 to 40 mm. Tests have shown that the stent to be applied does normally not have to exceed an outside diameter of approx. 5 mm in the expanded state.

The inner part is arranged in prolongation of a shaft of the applicator. The transition between the shaft and the inner part is smooth or tangentially rounded or also arcuate. The shaft is elastically deformable during normal use. After the deformation, the distal end of the malleable inner part can have an orientation that deviates significantly from the longitudinal axis of the inner part at its proximal end, i.e. from the longitudinal axis of the shaft. The deviation, i.e. the enclosed angle between the distal end and the proximal end of the inner part can range up to $70^{0}$.

In an advantageous refinement of the invention, the outer tube is dimensionally stable at least in the area of the length of the malleable inner part. The outer tube, like the inner part, can be deformed by manual force. Both components can preferably be deformed together by manual force. The dimensional stability is achieved by also making the outer tube of a material that is plastically malleable. At least in the forward section to be bent, the outer tube can be made of a different material than in its remaining regions. The outer tube can be made of a different material than the inner part and/or the shaft. At locations, where the outer tube does not have to be plastically deformable, it is then also preferably not. It is preferably elastically deformable there.

The plastic deformability of the outer tube and inner part ensures that the annular gap arranged between the inner side of the outer tube and the outer side of the inner part is not narrowed unevenly, which could interfere with the release of the stent. The annular gap preferably has an essentially constant diameter, so that the application is not impeded by a clamping between outer tube and inner part.

For an atraumatic application, the applicator has a preferably rounded tip at its outermost distal end. This tip should have a diameter of 1.9 to 2.6 mm. The stent itself should preferably be crimped to a diameter of 1 to 2.5 mm, in particular to match the diameter of the rounded tip.

The plastically malleable inner part is made in particular of a metal, in particular of a metal tube, with a thickening in the form of an olive at the tip. The stent is crimped onto the area of the inner part, which area adjoins the olive and has a reduced diameter, and is secured with the outer tube of the applicator. Before the procedure, the user can bend the involved area of the inner part which area is reduced in diameter.

The shaft of the applicator preferably has a diameter of 1.8 to 2.3 mm. It can additionally have a working channel with a diameter of smaller than or equal to 0.8 mm. The working channel can be used to place a moveable optical fiber in the working channel or to insert it into the working channel. An optical fiber is used to control the position of the distal end of the applicator or the stent before the stent is released. The optical fiber can be used in accordance with a diaphanoscopy. The optical fiber can also be advanced prior to release of the stent. The optical fiber is connected to an external light guide source. An optical fiber can be securely integrated into the applicator and as such represents a luminescent component for positional control before and during the procedure.

The anatomy, i.e. the position, the course and the length of the Eustachian tube can be determined prior to the procedure. In view of the flexible design of the applicator and a suitable stent selection, individual adaptation to the patient's anatomy is possible.

Stable handling of the applicator is possible despite the slight diameter. The applicator is so stable that, for example, a nasal spur would not twist the system during the procedure. A shaft made of high-quality steel with the stated thickness of 1.8 to 2.3 mm is sufficient to ensure sufficient strength and rigidity for stable handling. The use of guide wires for placement security is possible in view of an inner working channel with a diameter of smaller than or equal to 0.8 mm, which preferably extends over the entire system. As an alternative, a luminescent component for positional control can be used.

In combination with a dimensionally stable sluice that protects the stent, i.e. with a combination of outer tube and inner part, friction-free stent release can be guaranteed despite the distal curvature. In particular, a friction-free stent release is also possible even when both the inner part and the outer tube are bent into the desired coaxially running position through plastic deformation using manual force.

The applicator according to the invention is used with a stent made of a material with super-elastic material properties, namely with a stent made of nitinol. In the crimped state, such a self-expanding nitinol stent can have a diameter of 1 to 2.5 mm. The wall thickness can range from 0.09 to 0.15 mm. The radial forces of the stent can be adjusted by the wall thickness and also by the diameter of the stent. When the force is too low, the tube dysfunction will not be opened. Too much force will result in a gaping tube. The correct setting shall maintain the valve function of the tubes, i.e. support the musculature and facilitate the passive opening of the tube in the event of great pressure differentials.

In particular, the stent used has a closed-cell design. Such a design enables guidance of the stent around a curved path, as is adjustable by the applicator according to the invention.

The stent conforms to the anatomy of a Eustachian tube. For this purpose, it has a first end and a second end, with the ends having different diameters. A first end designed for placement on the tubal ostium has a diameter of 4.5 to 5.5 mm, preferably a diameter of 4.8 to 5.2 mm. In a particularly preferred exemplary embodiment, the diameter at the tubal ostium is 5 mm.

The second end designed for placement on the bony isthmus has a smaller diameter that is in a range from 2.5 to 3.5 mm, in particular in a range of 2.8 to 3.2 mm. In a particularly preferred exemplary embodiment, the diameter of the second end is 3 mm.

The transition from the region with greater diameter to the region with smaller diameter is established via a length portion which decreases in diameter. This length portion extends over 20 to 40% of the length of the stent, preferably over a range of 25 to 35%. In a particularly preferred exemplary embodiment, the length portion extends over a length of 30% of the length of the stent. This length section, which is reduced in diameter, is in particular of conical configuration. With a length of the stent of 8 to 40 mm, the length of the length portion that is reduced in diameter is approximately 3 to 12 mm, preferably 4 to 9 mm.

BRIEF DESCRIPTION OF THE DRAWING

The invention is explained hereinafter with reference to exemplary embodiments that are shown purely schematically in the drawings. It is shown in.

DETAILED DESCRIPTION OF PREFERRED EMBODIMENTS

Figure 1:
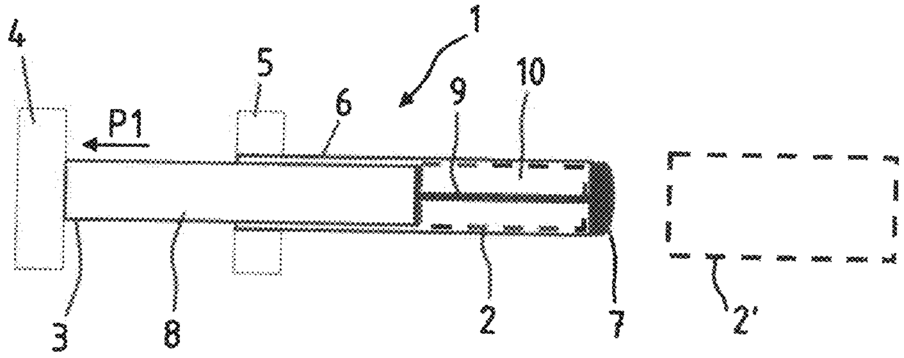
FIG. 1 a schematic illustration of an applicator.

FIG. 1 shows the greatly simplified applicator 1 for placing a stent 2 in a Eustachian tube, not shown in greater detail. At its proximal end 3, the applicator 1 has a widened stop 4 for a handle 5 which is attached to an outer tube 6 of the applicator 1. The handle 5 can be moved to the stop 4 in the direction of the arrow P1. As a result, the stent 2, which is held inside the outer tube 6, can be released at the distal end 7 of the applicator. The stent is made of nitinol. It is self-expanding. The released stent is shown purely symbolically in its expanded form with reference number 2'.

The applicator 1 has a long, slender shaft 8, which is shown in shortened form. It can have a longitudinal channel extending over the entire length. In the area of the distal end 7, there is a region on the shaft 8 with a reduced diameter. This involves an inner part 9 that is located in the outer tube 6 which is displaceable in longitudinal direction. The diameter in the inner part 9 is reduced to such an extent that the stent 2 can be placed in an annular space 10 prior to its release. The annular space 10 can also be referred to as a sluice. The inner part 9 and the outer tube 6 can be deformed by manual force.

Figure 2:
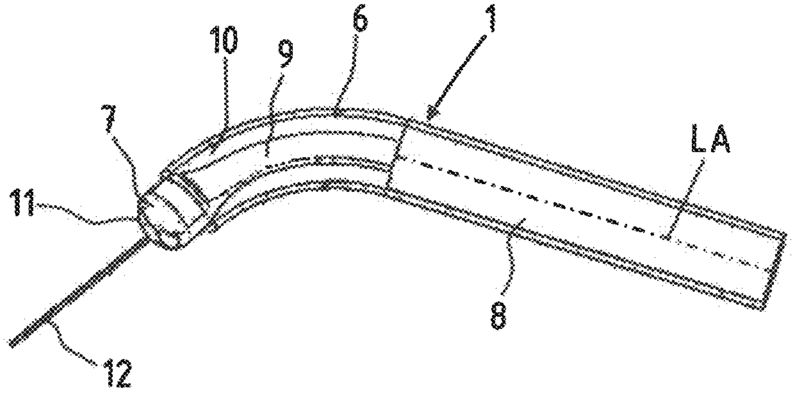
FIG. 2 a second illustration of an applicator with a curved tip.

The exemplary embodiment in FIG. 2 shows such an applicator 1 with a malleable inner part 9. The reference signs introduced for FIG. 1 are also retained for FIG. 2 for the designation of components that are essentially functionally the same. As in the exemplary embodiment in FIG. 1, the shaft 8 is surrounded by the outer tube 6, which in turn can be displaced in the direction of the longitudinal axis LA of the shaft 8. The stent can be arranged in the annular space 10. The distal end 7 has a rounded tip 11.

This applicator 1 is provided with a longitudinal channel which extends through the applicator 1 over the entire length. A light guide is arranged within the longitudinal channel. The light guide is connected to a light source. As a result, a light beam 12 can exit at the tip 11. The deformable area of the applicator can be bent by up to 70° in relation to the longitudinal axis LA in the non-bent length area of the applicator 1.

The forward region of the applicator, i.e. the inner part 9 and the region of the outer tube 6 there, are curved in an arc. The bend has been implemented using manual force. In addition, it can be seen that the outer tube 6 follows the bend of the inner part 9 essentially coaxially, so that the annular space 10 has an essentially constant cross section.

Figure 3:
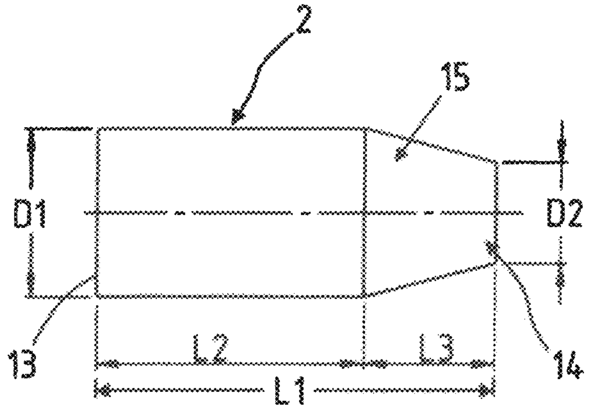
FIG. 3 a side view of a stent for use with the applicator according to the invention.
Figure 4:
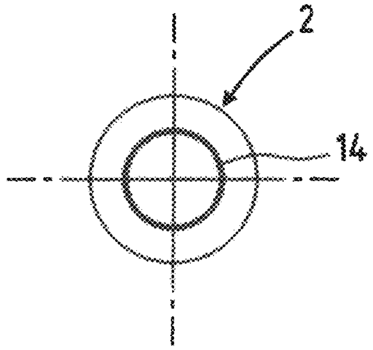
FIG. 4 an end view of the stent of FIG. 3.

An exemplary embodiment of a stent 2, which is preferably used with such an applicator 1, is shown in FIG. 3. It has a length L1. A cylindrical length portion with the length L2 extends over two-thirds of the length L1 of the stent 2. It is followed by a length portion 15 that becomes smaller in diameter with a length L3, which extends over a third of the length L1 of the stent 2. The diameter D1 on the left in the image plane, i.e. at the first end 13, is therefore greater than at the opposite second end 14. The larger diameter D1 is e.g. 5 mm and the smaller diameter D2 3 mm. The total length L1 of the stent 2 is 12 mm in this exemplary embodiment. FIG. 4 shows an end view of the stent 2 of FIG. 3 onto the second end 14 with a reduced diameter.

What is claimed is:

1. A system, comprising:

a stent including a first end designed for arrangement on a tubal ostium and having a diameter of 4.5 to 5.5 mm, a second end designed for arrangement on a bony isthmus and having a diameter which is smaller than a diameter of the first end and ranging from 2.5 mm to 3.5 mm, and adjacent to the second end a length portion which decreases in diameter and extends over 20% to 40% of a total length of the stent; and an applicator for placing the stent in a Eustachian tube, said applicator having a proximal end for handling the applicator and a distal end for receiving the stent, said distal end including an inner part which has at least one area that is plastically deformable by manual force, for adaptation to a patient-dependent access angle of the Eustachian tube, and an outer tube which surrounds the inner part at a radial distance and which delimits an annular gap for receiving the stent, with the stent in the annular gap made of nitinol and being self-expanding, wherein the stent comprises a length having the diameter of the first end and extending from the first end to the length portion which decreases in diameter, with the length portion decreasing in diameter from the diameter of the first end to the diameter of the second end; and wherein the length having the diameter of the first end is a cylindrical length portion and the length portion which decreases in diameter is conical and provides a transition from the diameter of the first end to the diameter of the second end.

2. The system of claim 1, wherein the inner part has a length of 20 to 40 mm.

3. The system of claim 1, wherein the distal end of the inner part has an orientation which deviates from a longitudinal axis of the applicator by up to 70°.

4. The system of claim 1, wherein the outer tube is made of a plastically deformable material at least in a region of the inner part.

5. The system of claim 1, wherein the applicator includes a rounded tip with a diameter of 1.9 to 2.6 mm.

6. The system of claim 1, wherein the applicator includes a shaft made of steel.

7. The system of claim 6, wherein the shaft has a diameter of 1.8 to 2.3 mm.

8. The system of claim 1, wherein the applicator includes a working channel with a diameter of smaller than or equal to 0.8 mm.

9. The system of claim 2, wherein the applicator includes a movable optical fiber arranged in the inner part for position control before releasing the stent.

10. The system of claim 1, wherein the stent has an adjustable crimping diameter of 1 to 2.5 mm.

11. The system of claim 1, wherein the stent has a wall thickness in a range from 0.09 to 0.15 mm.

12. The system of claim 1, wherein the stent has a closed-cell design and is guidable about a curved path.

13. The system of claim 1, wherein the stent has a total length of 8 to 40 mm.

* * * * *